United States Patent [19]

Bays et al.

[11] Patent Number: 4,650,810
[45] Date of Patent: Mar. 17, 1987

[54] INDOLE-5-ACETAMIDES FOR TREATMENT OF MIGRAINE

[75] Inventors: David E. Bays, Ware; Colin F. Webb, Royston; Michael D. Dowle, Ware, all of United Kingdom

[73] Assignee: Glaxo Group Limited, United Kingdom

[21] Appl. No.: 461,233

[22] Filed: Jan. 26, 1983

Related U.S. Application Data

[63] Continuation of Ser. No. 292,021, Aug. 11, 1981, abandoned.

[30] Foreign Application Priority Data

Aug. 12, 1980 [GB] United Kingdom ............... 8026286

[51] Int. Cl.$^4$ .................. A61K 31/40; C07D 209/14
[52] U.S. Cl. ................... 514/415; 514/212; 514/323; 514/414; 548/504; 546/204; 540/602
[58] Field of Search .................. 548/504, 494, 507; 546/201; 260/245.7; 514/212, 323, 414, 415

[56] References Cited

U.S. PATENT DOCUMENTS 3,472,870 10/1969 Larsen et al. ................. 548/504
4,252,803 2/1981 Webb ......................... 548/504

OTHER PUBLICATIONS

Burger, Alfred, *Medicinal Chemistry*, vol. II, Wiley-Interscience, New York (1970) pp. 1037–1039, 1224–1226.
Espamer, V., "Gramine Derivatives Antagonistic to 5-Hydroxytryptamine," Science 121 (1955) pp. 369–370.
Shaw, et al., "New Agents Inhibitory to the Pressor Effects of Serotonin," Chem. Abst. 50:14127(h) 19.

*Primary Examiner*—Glenna M. Hendricks
*Attorney, Agent, or Firm*—Bacon & Thomas

[57] ABSTRACT

Compounds are disclosed of general formula (I):

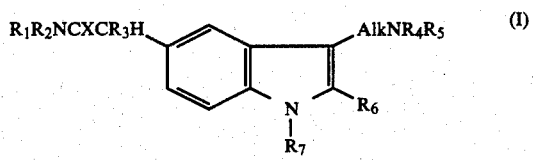

wherein $R_1$, $R_3$, $R_4$, $R_6$ and $R_7$, which may be the same or different, each represents a hydrogen atom or an alkyl group;

$R_2$ represents a hydrogen atom or an alkyl, aryl, aralkyl, cycloalkyl or alkenyl group;

or $R_1$ and $R_2$, together with the nitrogen atom to which they are attached, form a saturated monocyclic 5 to 7-membered ring which may optionally contain a further hetero function;

$R_5$ represents a hydrogen atom or an alkyl or alkenyl group;

or $R_4$ and $R_5$ together form an aralkylidene group;

Alk represents an alkylene chain containing two or three carbon atoms which may be unsubstituted or substituted by not more than two $C_{1-3}$ alkyl groups; and X represents an oxygen or sulphur atom; and physiologically acceptable salts, solvates and bioprecursors thereof. The compounds are described as potentially useful for the treatment of migraine and may be formulated as pharmaceutical compositions in conventional manner using one or more pharmaceutically acceptable carriers or excipients. Various processes for the preparation of the compounds are disclosed including, for example, a process involving reacting an indole having an appropriate nitrile group at the 5-position, with a suitable oxygen- or sulphur-containing compound in order to introduce the required amide or thioamide group at the 5-position on the indole nucleus.

10 Claims, No Drawings

INDOLE-5-ACETAMIDES FOR TREATMENT OF MIGRAINE

This application is a continuation of application Ser. No. 292,021, filed Aug. 11, 1981 now abandoned.

This invention relates to heterocyclic compounds, to processes for their preparation, to pharmaceutical compositions containing them and to their medical use.

The present invention provides an indole of the general formula (I):

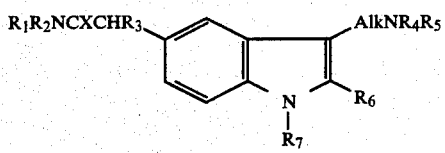

wherein
$R_1$, $R_3$, $R_4$, $R_6$ and $R_7$, which may be the same or different, each represents a hydrogen atom or an alkyl group;
$R_2$ represents a hydrogen atom, or an alkyl, aryl, aralkyl, cycloalkyl or alkenyl group;
or $R_1$ and $R_2$ together with the nitrogen atom to which they are attached, form a saturated monocyclic 5 to 7-membered ring which may optionally contain a further hetero function;
$R_5$ represents a hydrogen atom or an alkyl or alkenyl group;
or $R_4$ and $R_5$ together form an aralkylidene group;
Alk represents an alkylene chain containing two or three carbon atoms which may be unsubstituted or substituted by not more than two $C_{1-3}$ alkyl groups; and
X represents an oxygen or a sulphur atom, and physiologically acceptable salts, solvates (e.g. hydrates) and bioprecursors thereof.

The compounds according to the invention include all optical isomers thereof and their racemic mixtures.

Referring to the general formula (I), the alkyl groups may be straight chain or branched chain alkyl groups and they preferably contain from 1 to 6 carbon atoms. The cycloalkyl groups preferably contain 5 to 7 carbon atoms. The aryl groups themselves or the aryl moiety of the aralkyl groups are preferably phenyl groups which may optionally be substituted by one or more substituents selected from alkyl, hydroxy and alkoxy groups e.g. methoxy, and halogen atoms e.g. fluorine or chlorine. The alkyl moiety of the aralkyl groups preferably contains 1 to 4 carbon atoms. The alkenyl groups preferably contain 3 to 6 carbon atoms. The further hetero function of the saturated monocyclic 5 to 7-membered ring may be, for example, an oxygen atom or the group $NR_8$ (where $R_8$ is a hydrogen atom or a lower alkyl group).

Suitable physiologically acceptable salts of the indoles of general formula (I) include acid addition salts formed with organic or inorganic acids, for example hydrochlorides, hydrobromides, sulphates, fumarates and maleates. Other salts may be useful in the preparation of compounds of formula (I), e.g. creatinine sulphate adducts.

The term "bioprecursor" used herein means compounds which have a structure different from that of the compounds of formula (I) but which, upon administration to an animal or human being, are converted in the body to a compound of formula (I).

The compounds of the invention mimic methysergide in contracting the dog isolated saphenous vein strip (E. Apperley et al., Br. J. Pharmacol., 1980, 68, 215–224) and, like methysergide, they have little effect on blood pressure in the DOCA hypertensive rat. Methysergide is known to be useful in the treatment of migraine and produces a selective increase in carotid vascular resistance in the anaesthetised dog; it has been suggested (P. R. Saxena., Eur. J. Pharmacol., 1974, 27, 99–105) that this is the basis of its efficacy. Those compounds which we have tested show a similar effect in the anaesthetised dog and the compounds according to the invention are thus potentially useful for the treatment of migraine.

Accordingly, the invention also provides a pharmaceutical composition adapted for use in human medicine which comprises at least one compound of formula (I), a physiologically acceptable salt, solvate (e.g. hydrate) or bioprecursor thereof and formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The compounds of the invention may be formulated for parenteral administration by injection, including using conventional catheterisation techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral or buccal administration to man for the treatment of migraine is 0.1 to 100 mg of the active ingredient per unit dose which could be administered, for example 1 to 4 times per day.

Aerosol formulations are preferably arranged so that each metered dose or 'puff' of aerosol contains 20 µg–1000 µg of a compound of the invention. The overall daily dose with an aerosol will be within the range 100 µg–10 mg. Administration may be several times daily, for example 2, 3, 4 or 8 times, giving for example 1, 2 or 3 doses each time. The overall daily dose and the metered dose delivered by capsules and cartridges in an inhaler or insufflator could be double those with aerosol formulations.

A preferred class of compounds represented by the general formula (I) is that wherein $R_1$ represents a hydrogen atom and $R_2$ represents a hydrogen atom or an alkyl group containing 1 to 3 carbon atoms, e.g. methyl. Another preferred class of compounds is that in which $R_3$ represents a hydrogen atom.

A further preferred class of compounds is that wherein, in the general formula (I), Alk is an unsubstituted alkylene group containing two carbon atoms. A still further preferred class of compounds is that in which $R_4$ and $R_5$, which may be the same or different, each represents a hydrogen atom or a methyl or ethyl group and $R_6$ and $R_7$, each represents a hydrogen atom. It is preferred that the total number of carbon atoms in $R_4$ and $R_5$ together does not exceed two.

Compounds of general formula (I) in which X represents an oxygen atom are also preferred.

A preferred class of compounds of the invention is that represented by the general formula (Ia)

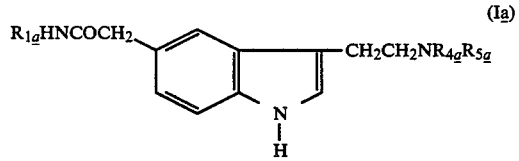

wherein
$R_{1a}$ represents a hydrogen atom or an alkyl group containing 1 to 4 carbon atoms e.g. methyl, ethyl or isopropyl; and
$R_{4a}$ and $R_{5a}$, which may be the same or different, each represents a hydrogen atom or a methyl or ethyl group, such that the total number of carbon atoms in $R_{4a}$ and $R_{5a}$ together does not exceed two, or together $R_{4a}$ and $R_{5a}$ represent a benzylidene group, and physiologically acceptable salts, solvates (e.g. hydrates) and bioprecursors thereof.

Particularly preferred compounds according to the invention include 3-(2-aminoethyl)-1H-indole-5-acetamide and 3-(2-aminoethyl)-N-methyl-1H-indole-5-acetamide and their physiologically acceptable salts, solvates (e.g. hydrates) and bioprecursors.

According to another aspect of the invention, compounds of formula (I), and physiologically acceptable salts, solvates (e.g. hydrates) or bioprecursors thereof, may be prepared by the general methods outlined below. In the following processes, $R_1$, $R_2$, $R_3$, $R_4$, $R_5$, $R_6$, $R_7$, X and Alk are as defined for the general formula (I) unless otherwise specified.

According to one general process (A), a compound of general formula (I) wherein X is an oxygen atom, may be prepared by condensing an amine of formula $R_1R_2NH$ with an acid of general formula (II):

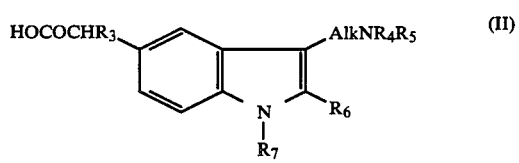

or an acylating agent corresponding thereto, or a salt (for example an organic or inorganic acid addition salt such as the hydrochloride, hydrobromide, sulphate or maleate salt, or creatinine sulphate adduct) or a protected derivative thereof.

The reaction involving condensation of the amine $HNR_1R_2$ with the acid of general formula (II) is desirably conducted in the presence of a coupling agent, for example carbonyl diimidazole or N,N'-dicyclohexylcarbodiimide. The condensation reaction may be carried out in a suitable reaction medium such as a haloalkane (e.g. dichloromethane), a nitrile (e.g. acetonitrile) or an amide (e.g. NN-dimethylformamide) conveniently at a temperature of from $-5°$ to $+30°$ C. The reaction may also be carried out in the absence of a coupling agent in a suitable reaction medium such as a hydrocarbon (e.g. toluene or xylene) conveniently at a temperature of from 50° to 120° C.

Acylating agents corresponding to the acid of general formula (II) which may be thus employed in the preparation of compounds of formula (I) include acid halides, for example acid chlorides. Such acylating agents may be prepared by reaction of an acid of general formula (II), or a salt or protected derivative thereof, with a halogenating agent such as phosphorus pentachloride, thionyl chloride or oxalyl chloride. Other suitable acylating agents which may be employed in the preparation of compounds of formula (I) include alkyl esters such as the methyl ester, activated esters (e.g. the 2-(1-methylpyridinyl) ester) and mixed anhydrides (e.g. formed with a haloformate, such as a lower alkylhaloformate).

The condensation process involving the acylating agents may be effected in a suitable reaction medium which may be aqueous or non-aqueous and conveniently at a temperature of from $-70°$ to $+150°$ C. Thus the condensation reaction using an acid halide, anhydride or activated ester may be effected in a suitable reaction medium such as an amide (e.g. N,N-dimethylformamide), an ether (e.g. tetrahydrofuran), a nitrile (e.g. acetonitrile), a haloalkane (e.g. dichloromethane) or mixtures thereof, optionally in the presence of a base such as pyridine or a tertiary amine and preferably at a temperature of from −5° to +25° C. The condensation reaction using an alkyl ester may be effected in a suitable reaction medium such as an alcohol (e.g. methanol), an amide (e.g. dimethylformamide), an ether (e.g. tetrahydrofuran) or mixtures thereof and conveniently at a temperature of from 0° to 100° C. In some instances, the amine $HNR_1R_2$ may itself act as reaction solvent.

Where it is desired to prepare a compound of formula (I) in which $R_1$ and $R_2$ are both hydrogen atoms, ammonia may be used in the form of aqueous ammonia or in a solvent such as methanol.

According to another general process (B) for preparing a compound of general formula (I) in which $R_1$ and $R_2$ are both hydrogen atoms, the group $-CXNH_2$ may be introduced by reacting a nitrile of general formula (III):

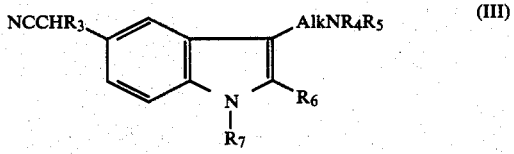 (III)

or a salt or protected derivative thereof, with a suitable oxygen- or sulphur-containing compound.

For example, in order to prepare a compound of general formula (I) wherein X is oxygen, a nitrile of general formula (III) may be hydrolysed with an acid or an alkali under controlled conditions. Thus, for example, the nitrile of formula (III) may be heated with concentrated sulphuric acid; concentrated hydrochloric acid; a mixture of concentrated sulphuric acid, acetic acid and water (1:1:1); polyphosphoric acid; sodium t-butoxide in refluxing t-butanol sodium hydroxide in aqueous ethanol in the presence of hydrogen peroxide; a base in the form of a resin or boron trifluoride in acetic acid.

According to another example, in order to prepare a compound of general formula (I) wherein X is sulphur, a nitrile of general formula (III) is heated at a temperature of from 20° to 115° C. with phosphorous pentasulphide in a solvent such as pyridine, or treated with hydrogen sulphide in dimethylformamide in the presence of triethylamine, conveniently at a temperature of from 20° to 100° C.

According to another general process (C), compounds of formula (I) may be prepared by the cyclisation of a compound of general formula (IV):

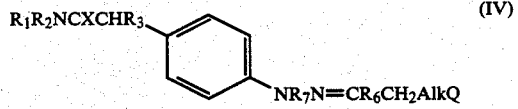 (IV)

wherein Q is the group $NR_4R_5$ (or a protected derivative thereof) or a leaving group such as halogen (e.g. chlorine), acetate, tosylate or mesylate.

Suitable cyclisation methods are referred to in 'A Chemistry of Heterocyclic Compounds—Indoles Part I', Chapter II, edited by W. J. Houlihan (1972) Wiley Interscience, New York. Particularly convenient embodiments of the process are described below.

When Q is the group $NR_4R_5$ (or a protected derivative thereof), the process is desirably carried out in an aqueous reaction medium, such as an aqueous alcohol (for example methanol) in the presence of an acid catalyst. (In some cases the acid catalyst may also act as the reaction solvent). Suitable acid catalysts include inorganic acids such as sulphuric or hydrochloric acid, organic carboxylic acids such as acetic acid. Alternatively the cyclisation may be carried out in the presence of a Lewis acid such as zinc chloride in ethanol or boron trifluoride in acetic acid. The reaction may conveniently be carried out at temperatures of from 20° to 200° C., preferably 50° to 125° C.

When Q is a leaving group such as chlorine the reaction may be effected in an aqueous organic solvent, such as an aqueous alcohol (e.g. methanol, ethanol or isopropanol), in the absence of a mineral acid, conveniently at a temperature of from 20° to 200° C., preferably 50° to 125° C. This process results in the formation of a compound of formula (I) wherein $R_4$ and $R_5$ are both hydrogen atoms.

In a particular embodiment of this process compounds of formula (I) may be prepared directly by the reaction of a compound of general formula (V):

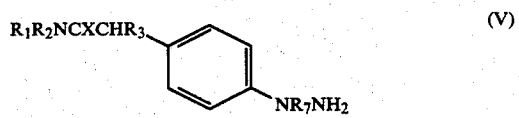 (V)

or a salt thereof, with a compound of formula (VI)

$R_6COCH_2AlkQ$ (VI)

wherein Q is as defined above or a salt or protected derivative thereof (such as an acetal or ketal e.g. formed with an appropriate alkyl orthoformate) using the appropriate conditions as described above.

Compounds of general formula (IV) may be isolated as intermediates during the process for the preparation of compounds of formula (I) wherein a compound of formula (V), or a salt or protected derivative thereof, is reacted with a compound of formula (VI), or a salt or protected derivative thereof, in a suitable solvent, such as an aqueous alcohol (e.g. methanol) at a temperature of, for example, from 20° to 30° C. If an acetal or ketal of a compound of formula (VI) is used, it may be necessary to carry out the reaction in the presence of an acid (for example, acetic or hydrochloric acid).

As illustrated in the following general processes (D) and (E) the aminoalkyl substituent $-AlkNR_4R_5$ may be introduced at the 3-position by a variety of conventional techniques which may, for example, involve modification of a substituent at the 3-position or direct introduction of the aminoalkyl substituent into the 3-position.

Thus a further general process (D) for preparing compounds of general formula (I) involves reacting a compound of general formula (VII)

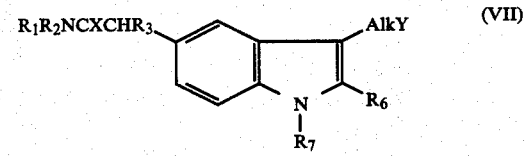 (VII)

(wherein Y is a readily displaceable group) or a protected derivative thereof, with an amine of formula $R_4R_5NH$.

The displacement reaction may conveniently be carried out on those compounds of formula (VII) wherein the substituent group Y is a halogen atom (e.g. chlorine, bromine or iodine) or a group OR where OR is, for example, an acyloxy group, such as acetoxy, chloroacetoxy, dichloroacetoxy, trifluoroacetoxy or p-nitrobenzoyloxy or a sulphonate group (e.g. p-toluene sulphonate).

The displacement reaction is conveniently effected in an inert organic solvent (optionally in the presence of water), examples of which include alcohols, e.g. ethanol; ethers, e.g. tetrahydrofuran; esters, e.g. ethyl acetate; amides, e.g. N,N-dimethylformamide; and ketones e.g. acetone, at a temperature of from $-10°$ to $+150°$ C., preferably 20° to 50° C.

The compounds of general formula (VII) wherein Y is a halogen atom may be prepared by reacting a hydrazine of general formula (V) with an aldehyde or ketone (or a protected derivative thereof) of formula (VI) in which Q is a halogen atom, in an aqueous alkanol (e.g. methanol) containing an acid (e.g. acetic or hydrochloric acid). Compounds of formula (VII) wherein Y is the group OR may be prepared from the corresponding compound wherein Y is a hydroxyl group by acylation or sulphonylation with the appropriate activated species (e.g. an anhydride or sulphonyl chloride) using conventional techniques. The intermediate alcohol may be prepared by cyclisation of a compound of formula (IV) wherein Q is a hydroxyl group (or a protected derivative thereof) under standard conditions.

Compounds of formula (I) may also be prepared by another general process (E) involving reduction of a compound of general formula (VIII):

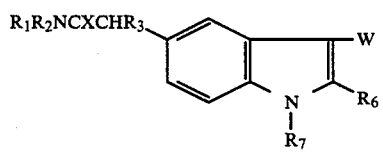

(VIII)

wherein W is a group capable of being reduced to give the required $AlkNR_4R_5$ group or a protected derivative thereof or a salt or protected derivative thereof.

The required Alk and $NR_4R_5$ groups may be formed by reduction steps which take place separately or together in any appropriate manner.

Groups which may be reduced to the group Alk include corresponding unsaturated groups and corresponding groups containing either a hydroxyl group or a carbonyl function.

Groups which may be reduced to the group $NR_4R_5$ where $R_4$ and $R_5$ are both hydrogen include nitro, azido, hydroxyimino and nitrile groups. In the latter case, reduction yields the group $CH_2NH_2$ and thus provides a methylene group of the group Alk.

The required $NR_4R_5$ group wherein $R_4$ and/or $R_5$ are other than hydrogen may be prepared by reduction of a nitrile $(CHR_9)_nCHR_{10}CN$ or an aldehyde $(CHR_9)_nCHR_{10}CHO$ (where $R_9$ and $R_{10}$, which may be the same or different, each represents a hydrogen atom or a $C_{1-3}$ alkyl group and n is zero or 1) in the presence of an amine, $R_4R_5NH$. Alternatively the $NR_4R_5$ group may be prepared by reaction of the corresponding compound wherein $R_4$ and/or $R_5$ represent hydrogen with an appropriate aldehyde or ketone in the presence of a suitable reducing agent. In some instances (e.g. for the introduction of the group $R_5$ where $R_5$ is benzyl) the aldehyde (e.g. benzaldehyde) may be condensed with the amine and the intermediate thus formed may subsequently be reduced using a suitable reducing agent.

Examples of suitable groups represented by the substituent W include the following: $TNO_2$ (where T is Alk or an alkenyl group corresponding to the group Alk); $AlkN_3$; $(CHR_9)_nCHR_{10}CN$; $(CHR_9)_nCOCHR_{10}Z$; $(CHR_9)_nCR_{10}=NOH$; or $CH(OH)CHR_{10}NR_4R_5$ (where $R_9$, $R_{10}$ and n are as previously defined, and Z is an azido group $N_3$ or the group $NR_4R_5$, or a protected derivative thereof).

It will be appreciated that the choice of reducing agent and reaction conditions will be dependent on the nature of the group W and the nature of other groups already present on the molecule.

Suitable reducing agents which may be used in the above process include hydrogen in the presence of a metal catalyst (except wherein X is S); or an alkali metal borohydride or cyanoborohydride, e.g. sodium borohydride or cyanoborohydride (except in general wherein W contains a nitrile or hydroxyimino group).

The metal catalyst may be, for example, Raney Nickel or a noble metal catalyst, such as platinum, platinum oxide, palladium or rhodium, which may be supported, for example on charcoal or kieselguhr. In the case of Raney nickel, hydrazine may also be used as the source of hydrogen.

Reduction in the presence of hydrogen and a metal catalyst may conveniently be carried out in a solvent such as an alcohol, e.g. ethanol; an ether, e.g. dioxan or tetrahydrofuran or an ester e.g. ethyl acetate and at a temperature of from $-10°$ to $+50°$ C., preferably $-5°$ to $+30°$ C. The alkali metal borohydride or cyanoborohydride reduction may conveniently be carried out in an alcohol such as propanol or ethanol and at a temperature of from 10° to 100° C. In some instances the reduction using borohydride may be carried out in the presence of cobaltous chloride.

Thus, in a particular embodiment of this process, a compound of formula (VIII) wherein W is the group $CHR_{10}CN$, $CHR_9CHR_{10}NO_2$, $CH=CR_{10}NO_2$ or $CHR_9CR_{10}=NOH$ may be reduced for example using hydrogen in the presence of a metal catalyst such as Raney nickel or palladium.

According to a second embodiment, a compound of formula (VIII), wherein W is the group $COCHR_{10}Z$ may be reduced preferably with heating using for example, sodium borohydride in propanol. According to a third embodiment of this process, a compound of formula (VIII), wherein W is the group $AlkN_3$ or $CH(OH)CHR_{10}NR_4R_5$, may be reduced for example using hydrogen in the presence of a catalyst such as palladium, or sodium borohydride. These reagents are also suitable for the reductive alkylation of, for example, $AlkNHR_5$ in the presence of a suitable aldehyde or ketone.

The starting materials or intermediate compounds of formula (VIII) may be prepared by analogous methods to those described in U.K. Published Patent Application No. 2035310, and 'A Chemistry of Heterocyclic Compounds-Indoles Part II', Chapter VI, edited by W. J. Houlihan (1972) Wiley Interscience, New York.

Compounds of formula (VIII), wherein W is the group $(CHR_9)_nCHR_{10}CHO$ may be prepared by oxidation (e.g. with Jones' reagent) of a compound of formula (VII) wherein Y is a hydroxyl group. A compound of formula (VIII) wherein W is the group $(CHR_9)_nCR_{10}$=NOH may be prepared by treatment of the corresponding aldehyde with hydroxylamine hydrochloride using standard conditions.

The intermediate compound of formula (VIII) wherein W is the group AlkN$_3$ may be prepared from a compound of formula (VII) wherein Y is a halogen atom using standard procedures.

Standard reducing agents such as sodium borohydride may be used to prepare a compound of formula (VIII) wherein W is the group CH(OH)CHR$_{10}$NR$_4$R$_5$ from the corresponding compound of formula (VIII) wherein W is the group COCHR$_{10}$NR$_4$R$_5$.

The following reactions (F), in any appropriate sequence, may if necessary and/or desired be carried out subsequent to any of the above described processes:

(i) conversion of one compound of general formula (I) or a salt or protected derivative thereof into another compound of general formula (I);

(ii) removal of any protecting groups; and (iii) conversion of a compound of general formula (I) or a salt thereof into a physiologically acceptable salt, solvate (e.g. hydrate) or bioprecursor thereof.

Thus, a compound of formula (I) according to the invention may be converted into another compound of formula (I) using conventional techniques. For example, a compound of general formula (I) wherein X is sulphur may be prepared from the corresponding compound of formula (I) wherein X is oxygen, by reaction with a suitable sulphur-containing compound such as phosphorus pentasulphide. The reaction may be effected in an organic solvent medium, such as pyridine, at a temperature of from 20° to 115° C.

According to another example, a compound of general formula (I) wherein one or more of R$_1$, R$_2$, R$_4$, R$_5$ and R$_7$ are alkyl groups may be prepared from the corresponding compounds of formula (I) wherein one or more of R$_1$, R$_2$, R$_4$, R$_5$ and R$_7$ represent hydrogen, by reaction with a suitable alkylating agent, such as an alkyl halide, alkyl tosylate or dialkylsulphate. The alkylation reaction is conveniently carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides, such as sodium hydride, alkali metal amides such as sodium amide, alkali metal carbonates, such as sodium carbonate or an alkali metal alkoxide such as sodium or potassium methoxide, ethoxide or t-butoxide.

A particularly suitable method for preparing a compound of formula (I) wherein R$_4$ and/or R$_5$ is other than hydrogen, is reductive alkylation of the corresponding compound wherein R$_4$ and/or R$_5$ represent hydrogen, with an appropriate aldehyde or a ketone (e.g. acetone) in the presence of a suitable reducing agent. Alternatively the aldehyde or ketone may be condensed with the primary amine and the intermediate thus formed may subsequently be reduced using a suitable reducing agent. It will be appreciated that the choice of reducing agents and reaction conditions depends upon the nature of the substituent groups already present on the compound of formula (I) which is to be alkylated. Suitable reducing agents which may be employed in this reaction include hydrogen in the presence of a metal catalyst, an alkali metal borohydride or cyanoborohydride (e.g. sodium borohydride or cyanoborohydride) using the conditions previously described or formic acid (using the carbonyl compound as reaction solvent, at a temperature of from 0°–100° C., conveniently 0°–50° C.).

It should be appreciated that in some of the above transformations it may be necessary or desirable to protect any sensitive groups in the molecule of the compound in question to avoid undesirable side reactions. For example, during any of the reaction sequences described above, it may be necessary to protect the group NR$_4$R$_5$, wherein R$_4$ and/or R$_5$ represent hydrogen, with a group easily removable at the end of the reaction sequence. Such groups may include, for example, aralkyl groups, such as benzyl, diphenylmethyl or triphenylmethyl; or acyl groups, such as N-benzyloxycarbonyl or t-butoxycarbonyl or phthaloyl.

In some cases, it may also be necessary to protect the indole nitrogen wherein R$_7$ is hydrogen.

Subsequent cleavage of the protecting group may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

Where it is desired to isolate a compound of the invention as a salt, for example as an acid addition salt, this may be achieved by treating the free base of general formula (I), with an appropriate acid, preferably with an equivalent amount or with creatinine sulphate in a suitable solvent (e.g. aqueous ethanol).

The starting materials or intermediate compounds for the preparation of the compounds according to this invention may be prepared by analogous methods to those described in U.K. Published Patent Application No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced before or after cyclisation to form the indole nucleus. It should therefore be appreciated that in such multi-stage processes, the sequence of reactions should be chosen in order that the reaction conditions do not affect groups present in the molecule which are desired in the final product.

The invention is further illustrated by the following Examples. All temperatures are in °C.

EXAMPLE 1

3-(2-Aminoethyl)-1H-indole-5-acetamide, compound with creatinine, sulphuric acid and water (1:1:1.1:2)

(i) 3-[2-(1,3-Dihydro-1,3-dioxo-2H-isoindol-2-yl)ethyl]-1H-indole-5-acetic acid

A solution of 4-(1,3-dihydro-1,3-dioxo-2H-isoindol-2-yl)butanal, diethyl acetal (36 g) in absolute ethanol (125 ml) was added to a solution of 4-hydrazinobenzene acetic acid, hydrochloride (25 g) in 25% aqueous acetic acid (640 ml) heated to 80° under nitrogen. The mixture was heated at 70°–80° for 2.75 h and the solvent was removed under reduced pressure to give a red oil. This was diluted with water and extracted with ethyl acetate (5×250 ml). A gummy solid insoluble in either phase was collected and triturated with ethanol to give the title compound as a beige solid (7.4 g). The organic extracts were dried (MgSO$_4$) and concentrated to an oil which was taken up in chloroform and treated with diethyl ether to give a second crop as a yellow solid (13.1 g). A sample (0.5 g) of this material was purified by column chromatography (Whatman MFC silica, 25 g) and elution with ethyl acetate—light petroleum (1:1) gave the title compound as a yellow solid (0.35 g) m.p. 189°–191.5°.

(ii) 3-[2-(1,3-Dihydro-1,3-dioxo-2H-isoindol-2-yl)ethyl]-1H-indole-5-acetic acid, methyl ester A solution of 3-[2-(1,3-dihydro-1,3-dioxo-2H-isoindol-2-yl)ethyl]-1H-indole-5-acetic acid (1 g) in methanol (50 ml) containing sulphuric acid (2 drops) was boiled under reflux for 1.5 h under nitrogen. Removal of the solvent gave a solid (1.2 g). Part of this material (0.5 g) was purified by column chromatography (Whatman MFC silica, 25 g). Elution with ethyl acetate-light petroleum (1:1) gave the title compound as yellow crystals (0.4 g) m.p. 121°–124°.

(iii) 3-(2-Aminoethyl)-1H-indole-5-acetic acid, methyl ester, compound with creatinine, sulphuric acid and water (1:1:1:1.25)

A solution of 3-[2-(1,3-dihydro-1,3-dioxo-2H-indol-2-yl)ethyl]-1H-indole-5-acetic acid, methyl ester (1.4 g) in ethanol (75 ml) was stirred at room temperature under nitrogen with 33% ethanolic methylamine (15 ml) for 1.5 h. The solvent was removed under reduced pressure and the residual brown oil was purified by column chromatography (Whatman MFC, silica, 100 g). Elution with ethyl acetate:propan-2-ol:water:ammonia (25:15:8:2) gave the tryptamine (0.2 g) and a second crop (0.4 g) contaminated with a non-basic impurity. This material was treated with creatinine sulphate (0.56 g) in aqueous ethanol to give a white solid which was recrystallised twice from aqueous ethanol to give the title compound (0.15 g) m.p. 215°–217.5°.

(iv) 3-(2-Aminoethyl)-1H-indole-5-acetamide, compound with creatinine, sulphuric acid and water (1:1:1.1:2)

3-(2-Aminoethyl)-1H-indole-5-acetic acid, methyl ester (9 g) was suspended in aqueous ammonia (d 0.88, 1 liter) and the mixture was stirred at room temperature under nitrogen for 80 h. The mixture was filtered to remove a tacky solid, and the filtrate was evaporated to dryness under reduced pressure to give a yellow solid (B 5.4 g), which was purified by column chromatography (Merck Kieselgel 60 silica, 60 g). Elution with ethyl acetate:propan-2-ol:water:ammonia (25:15:8:2) gave a brown oil (4.1 g) which was purified further by chromatography to give the indole-5-acetamide as a yellow oil (1:1 g). This was taken up in aqueous ethanol and treated with a 2M aqueous solution of creatinine and sulphuric acid (1:1) (1.48 ml) to give a white solid. Recrystallisation from aqueous ethanol gave the title compound as white microcrystals (0.6 g), m.p. 244°–246°.

Analysis found: C, 40.45; H, 5.42; N, 17.43; S, 7.56; C$_{12}$H$_{15}$N$_3$O.C$_4$H$_7$N$_3$O.1.1H$_2$SO$_4$.2H$_2$O requires: C, 40.52; H, 5.95; N, 17.73; S, 7.43%.

EXAMPLE 2

3-(2-Aminoethyl)-1H-indole-5-acetamide, hydrochloride (i) 2-(4-Hydrazinophenyl)acetamide hydrochloride To a stirred suspension of 2-(4-aminophenyl)acetamide (19.5 g) in concentrated hydrochloric acid (43 ml) was added an ice cold solution of sodium nitrite (9.43 g) in water (25 ml) at such a rate that the temperature of the mixture remained between −5° and +5° C. When the addition was complete the solution was stirred at 0° C. for 15 min. This was then added to a stirred solution of stannous chloride (146.3 g) in concentrated hydrochloric acid (86 ml) at −10° C. The mixture was stirred for 30 min., poured into ice cold ethanol (750 ml) and the suspension was stirred for a further 30 min. Collection of the solid by filtration and washing with ethanol followed by ether gave the title compound as a white powder (20.6 g). This material was 62% pure but was contaminated with sodium chloride. It was used in the next stage without further purification.

(ii) 3-[2-(1,3-Dihydro-1,3-dioxo-2H-isoindol-2-yl)ethyl]-1H-indole-5-acetamide

A mixture of the crude 2-(4-hydrazinophenyl)acetamide hydrochloride (16.19 g) (contains 0.05 mol) and 4-(1,3-dihydro-1,3-dioxo-2H-isoindol-2-yl)butanal diethyl acetal (14.5 g) was heated under reflux in 25% aqueous acetic acid (1 l) for 30 min. The cooled mixture was poured into ethyl acetate (750 ml) the organic phase was separated and the aqueous phase was washed with ethyl acetate (250 ml). The combined organic extracts were washed with water (500 ml), dried (Na$_2$SO$_4$) and evaporated under reduced pressure. Water (500 ml) was added to the oily residue which solidified on stirring. The solid was collected by filtration, washed with water and dried. Crystallisation from ethyl acetate-methanol gave the title compound as pale yellow granules (11.9 g) m.p. 191°–3° C.

(iii) 3-(2-Aminoethyl)-1H-indole-5-acetamide hydrochloride

A solution of 3-[2-(1,3-dihydro-1,3-dioxo-2H-isoindol-2-yl)ethyl]-1H-indole-5-acetamide (8.0 g) in ethanol (500 ml) containing hydrazine hydrate (5.76 g), was heated under reflux for 2 h. The solvent was removed by evaporation, the residue was suspended in ethyl acetate (500 ml) and washed with saturated potassium carbonate solution (300 ml). The organic phase was separated and the aqueous phase again extracted with ethyl acetate (200 ml). Evaporation of the dried (Na$_2$SO$_4$) combined organic extracts gave an off-white solid. This was dissolved in ethyl acetate (90 ml) containing methanol (10 ml) and ethereal hydrogen chloride was added until no more solid deposited. Crystallisation from ethyl acetate-methanol gave the title compound as off-white granules (3.2 g) m.p. 225°–7° C.

Analysis Found: C, 55.85; H, 6.48; N, 16.04; C$_{12}$H$_{15}$N$_3$O.HCl.0.25H$_2$O Requires: C, 55.81; H, 6.44; N, 16.27%.

EXAMPLE 3

3-(2-Aminoethyl)-N-methyl-1H-indole-5-acetamide, compound with creatinine, sulphuric acid and water (1:1:1:1)

A solution of 3-[2-(1,3-dihydro-1,3-dioxo-2H-isoindol-2-yl)ethyl]-1H-indole-5-acetic acid, methyl ester (1.8 g) in 33% methylamine in ethanol solution (50 ml) was left to stand at room temperature for 18 h, then the solvent was removed under reduced pressure at room temperature. The resulting white foam was dissolved in aqueous ethanol and a 2M aqueous solution of creatinine and sulphuric acid (2.45 ml) (1:1) was added at 60° C. As the solution cooled, the title compound crystallised out as white microcrystals (0.75 g) m.p. 254°–257° (dec).

Analysis Found: C, 44.62; H, 5.84; N, 18.15%.
$C_{13}H_{17}N_3O.C_4H_7N_3O.H_2SO_4.H_2O$ requires: C, 44.34; H, 6.13; N, 18.25%.

EXAMPLE 4

3-[2-(Methylamino)ethyl]-1H-indole-5-acetamide compound with ether and water (6:1:5)

(i) 3-[2-[(Phenylmethyl)amino]ethyl]-1H-indole-5-acetamide compound with maleic acid (1:1)

Benzaldehyde (1.4 g) was added to 3-(2-aminoethyl)-1H-indole-5-acetamide (2.8 g), in a mixture of benzene and ethanol (5:1, 40 ml) at room temperature. The resulting solution was evaporated to dryness in vacuo after 2.5 h and the residue was dissolved in absolute ethanol (75 ml). Sodium borohydride (0.5 g) was added in portions over 10 min at room temperature with stirring. After 7 h at room temperature acetic acid (2 ml) was added and the mixture was stirred overnight and then evaporated. The residue was chromatographed on silica gel (Merck type 60, 260 g) eluting with methanol in chloroform (1–25%). The combined product-bearing fractions were evaporated and dissolved in chloroform (300 ml) and washed with 8% aqueous sodium hydrogen carbonate (2.75 ml). The chloroform solution was dried ($Na_2SO_4$), filtered and evaporated to give the tryptamine as a yellow glass (2.5 g).

A portion (0.2 g) of the glass was dissolved in methanol and a solution of maleic acid (0.076 g) in ether was added. A pasty solid precipitated. The solvent was decanted and replaced by ether. Scratching the mixture produced the title compound as a finely divided pale fawn solid which was collected and dried at 50° in vacuo (0.2 g) m.p. 130°–158° (bubbled from 80°).

(ii) 3-[2-[Methyl(phenylmethyl)amino]ethyl]-1H-indole-5-acetamide hemihydrate

A solution of methyl iodide (0.83 g) in tetrahydrofuran (50 ml) was added at room temperature to a solution of 3-[2-[(phenylmethyl)amino]ethyl]-1H-indole-5-acetamide (1.8 g) and diisopropylethylamine (0.76 g) in dry tetrahydrofuran (150 ml). The resulting solution was stirred at room temperature for 16 h and was then evaporated in vacuo to dryness. The residue was partitioned between chloroform (225 ml) and 8% aqueous sodium hydrogen carbonate (250 ml). The organic layer was run off and the aqueous layer extracted with more chloroform (200 ml). The combined organic solutions were dried ($Na_2SO_4$), filtered and evaporated to afford a gum (1.6 g) which was purified by column chromatography on silica gel (Merck Type 60, 250 g) eluting with methanol in chloroform (1–10%). The product-bearing fractions afforded the title compound as a pale yellow oil which slowly crystallised on standing 0.4 g m.p. 123°–126° (bubbles above 93°).

(iii) 3-[2-(Methylamino)ethyl]-1H-indole-5-acetamide compound with ether and water (6:1:5)

A mixture of 3-[2-[methyl(phenylmethyl)amino]ethyl]-1H-indole-5-acetamide (0.38 g) and 10% palladium on charcoal catalyst (50% aqueous paste 1.5 g) in absolute ethanol (50 ml) was stirred vigorously under a hydrogen atmosphere for 4 h. The catalyst was filtered off on a celite pad and the resulting clear colourless filtrate was evaporated in vacuo. The resulting colourless oil was evacuated to give a glass/paste mixture. Trituration of this material with ether produced a cream solid which was collected and dried in vacuo at 50° to give the title compound (0.18 g) m.p. 156°–160° (some bubbling at 100°–125°).

Analysis Found: C, 63.21; H, 7.88; N, 15.86; $C_{13}H_{17}N_3O.0.17C_4H_{10}O.0.83H_2O$ requires: C, 63.46; H, 7.92; N, 16.25%.

EXAMPLE 5

3-[2-(Phenylmethylideneamino)ethyl]-1H-indole-5-acetamide compound with ethanol and water (10:2:5)

A solution of benzaldehyde (0.6 g) in benzene (3 ml) was added to 3-(2-aminoethyl)-1H-indole-5-acetamide (1.2 g) at room temperature. The mixture was stirred and ethanol (2 ml) was added to dissolve completely the starting material. The solution was stirred for 2 days and was then stirred with charcoal for a further day. The charcoal was filtered off and the filtrate was evaporated. The resulting oil was triturated with benzene/ether (1:1). The solvent mixture was decanted and replaced by fresh solvent. The paste which was obtained was dried in vacuo, washed with boiling ether and re-dried to give the title compound as a pale fawn solid, (1.2 g) m.p. 144°–150°.

Analysis Found: C, 72.50; H, 6.38; N, 13.32; $C_{19}H_{19}N_3O.0.5H_2O.0.2C_2H_6O$ requires: C, 72.01; H, 6.60; N, 12.99%.

EXAMPLE 6

3-(2-Aminoethyl)-N-(1-methylethyl)-1H-indole-5-acetamide, compound with maleic acid (1:1)

(i) 3-[2-[[(Phenylmethoxy)carbonyl]amino]ethyl]-1H-indole-5-acetic acid

A solution of 3-[2-(1,3-dihydro-1,3-dioxo-2H-isoindol-2-yl)ethyl]-1H-indole-5-acetic (2.5 g) was heated at reflux with hydrazine hydrate (1.7 ml) in ethanol (60 ml) for 2½ h. The resulting suspension was cooled to ambient temperature, all the solvent was evaporated in vacuo, the resulting yellow solid dissolved in dilute sodium hydroxide (2N, 50 ml) and tetrahydrofuran (20 ml) and treated with benzyl chloroformate (3 ml) at 5°. Stirring was continued for 1 h at ambient temperature; the reaction mixture was poured onto dilute hydrochloric acid (2N, 100 ml), extracted with dichloromethane (3×200 ml), the organic layers were dried ($MgSO_4$) and solvent was removed to give a crude oily product. Column chromatography on silica (Merck 7734; 90 g), eluting with 3% methanol-dichloromethane, gave an oil which was triturated with ether to give the title compound as a white solid (0.78 g) m.p. 116°–7°.

(ii) Phenylmethyl[2-[5-[2-(1-methylethyl)amino]-2-oxoethyl]-1H-indol-3-yl]ethyl]carbamate To a solution of 3-[2-[[(phenylmethoxy)carbonyl]amino]ethyl]-1H-indole-5-acetic acid (1 g) and triethylamine (1.5 ml) in acetonitrile (40 ml), was added 2-chloro-1-methylpyridinium iodide (2 g) at room temperature and stirring was continued at ambient temperature for 2 h. To the resulting dark solution iso-propylamine (4 ml) was added (ambient temperature) and stirring was continued for an additional 2 h.

The solvent was evaporated and the residual oil was purified by column chromatography on silica (Merck 7734; 50 g) eluting with 2% methanoldichloromethane to give the title compound as a white solid (0.41 g) m.p. 140°–2°.

(iii) 3-(2-Aminoethyl)-N-(1-methylethyl)-1H-indole-5-acetamide, compound with maleic acid (1:1)

Phenylmethyl [2-[5-[2-(1-methylethyl)amino]-2-oxoethyl]-1H-indol-3-yl]ethyl]carbamate (0.5 g) was hydrogenated for 5 h in absolute ethanol (75 ml) over pre-reduced palladium on charcoal (0.2 g) (50% moistened paste) at atmospheric pressure. The catalyst was removed by filtration through Hyflo and removal of the solvent gave a white foam. This was taken up in ethanol (5 ml) and maleic acid (0.12 g) in ethanol (2 ml) was added. The solvent was removed in vacuo and the remaining oil was triturated with ethyl acetate and ethanol to give the title compound as a white solid (0.4 g), m.p. 137°–138°.

Analysis Found: C, 60.64; H, 6.86; N, 11.33%; $C_{15}H_{21}N_3O.C_4H_4O_4$ Requires: C, 60.79; H, 6.71; N, 11.19%.

EXAMPLE 7

3-(2-Aminoethyl)-N-phenyl-1H-indole-5-acetamide, compound with maleic acid and water (2:2:1)

(i) 3-[2-(1,3-Dihydro-1,3-dioxo-2H-isoindol-2-yl)ethyl]-N-phenyl-1H-indole-5-acetamide An ice-cold solution of diphenylamino carbonyl pyridinium chloride (3.5 g) in water (35 ml) was added dropwise to a mixture of 3-[2-(1,3-dihydro-1,3-dioxo-2H-isoindol-2-yl)ethyl]-1H-indole-5-acetic acid (3.5 g), triethylamine (2.8 ml) and ice-water (70 ml) with rapid stirring over 15 min. After stirring the mixture for a further 10 min. it was extracted with ethyl acetate (3×30 ml). The combined organic extracts were washed with water (1×50 ml), dried (Na₂SO₄) and evaporated in vacuo to give an orange solid (3.6 g).

This solid was dissolved in freshly distilled aniline (10 ml) by heating on a steam bath for 15 min. The solution was cooled, and was partitioned between ethyl acetate (100 ml) and aqueous hydrochloric acid (2N, 200 ml). The aqueous phase was separated, and extracted with a further portion of ethyl acetate (100 ml). The combined organic extracts were washed with water (100 ml), dried (Na₂SO₄) and evaporated in vacuo to give a yellow solid (4.1 g).

This solid was chromatographed over Kieselguhr 60 using ethyl acetate as eluant. The fractions containing product were combined, and the solvent was evaporated in vacuo to give the title compound as a white solid (1.5 g). A small portion (0.1 g) was crystallised from methanol to give a sample analytically pure, m.p. 231°–232°.

(ii) 3-(2-aminoethyl)-N-phenyl-1H-indole-5-acetamide, compound with maleic acid and water, (2:2:1)

3-[2-(1,3-Dihydro-1,3-dioxo-2H-isoindol-2-yl)ethyl]-N-phenyl-1H-indole-5-acetamide and hydrazine hydrate (0.83 g) in ethanol were heated at reflux for 4 h. The solution was cooled, and evaporated in vacuo. The residue was partitioned between ethyl acetate (50 ml) and a mixture of saturated aqueous potassium carbonate (60 ml) and water (40 ml). The aqueous phase was separated, and extracted with a further portion of ethyl acetate (40 ml). The combined organic extracts were washed with water (50 ml) dried (Na₂SO₄), and evaporated in vacuo to give a yellow oil (0.85 g).

A portion of this oil (0.69 g) was dissolved in ethanol (2 ml) and a solution of maleic acid (0.27 g) in ethyl acetate (4 ml) was added. The solution was diluted with ether, and an orange gum separated. The solvent was decanted and more ether (60 ml) was added.

The resulting solid was filtered off, and was dried at 60° C./0.1 torr for 18 h to give the title compound as a pale orange solid (0.67 g) m.p. 82°–86° C.

Analysis Found: C, 63.1; H, 5.6; N, 9.7; $C_{18}H_{19}N_3O.C_4H_4O_4.0.5H_2O$ requires: C, 63.1; H, 5.8; N, 10.0%.

EXAMPLE 8

3-(2-Aminoethyl)-N,N-dimethyl-1H-indole-5-acetamide, hydrochloride, hydrate (i) 2-(4-Aminophenyl)-N,N-dimethylacetamide A mixture of methyl 4-aminophenyl acetate (8.25 g) and 40% aqueous dimethylamine (50 ml) was stirred at 0° C. for 4 h and for a further 12 h at room temperature. The pale yellow solution was poured into 2N sodium carbonate (100 ml) and extracted with ethyl acetate (2×200 ml). Evaporation of the dried (Na₂SO₄) organic extracts gave a pale yellow oil. Crystallisation from ethyl acetatecyclohexane afforded the title compound as white microneedles (3.5 g) m.p. 100°–1° C.

(ii) 2-(4-Hydrazinophenyl)-N,N-dimethylacetamide, hydrochloride

An ice cold solution of sodium nitrite (1.088 g) in water (6 ml) was added to a stirred solution of 2-(4-aminophenyl)-N,N-dimethylacetamide (2.67 g) in concentrated hydrochloric acid (10 ml) at −5° C. After stirring the yellow solid for 15 min, it was added to a stirred solution of stannous chloride (16.88 g) in concentrated hydrochloric acid (10 ml) at −10° C. When the addition was complete, the mixture was stirred at room temperature for a further 30 min and poured into ethanol (100 ml). The mixture was evaporated to dryness under reduced pressure, basified using 2N sodium hydroxide (350 ml) and extracted with ethyl acetate (3×200 ml). Evaporation of the dried (Na₂SO₄) solvent gave a pale yellow gum which was dried under high vacuum. This was dissolved in ethyl acetate (50 ml) and ethereal hydrogen chloride was added until no more solid deposited. Collection of the solid by filtration and washing with ether gave the title compound as a white powder (1.45 g) which was 82.6% pure and was used in the next stage without further purification.

(iii) 3-[2-(1,3-Dihydro-1,3-dioxo-2H-isoindol-2-yl)ethyl]-N,N-dimethyl-1H-indole-5-acetamide A mixture of 2-(4-hydrazinophenyl)-N,N-dimethylacetamide hydrochloride (0.875 g, contains 0.00315 mol) and 4-(1,3-dihydro-1,3-dioxo-2H-isoindol-2-yl)butanal, diethyl acetal (0.873 g) was heated under reflux in 25% aqueous acetic acid (100 ml) for 30 min. The mixture was poured into ethyl acetate (150 ml) and the aqueous phase was separated. This was washed with ethyl acetate (150 ml) and the organic extracts were combined. The yellow solution was washed successively with water (150 ml) 8% sodium bicarbonate solution (150 ml) and finally water (150 ml). Evaporation of the dried (Na₂SO₄) solvent gave a yellow solid which crystallised from propan-2-ol to give the title compound as a pale yellow powder (0.91 g) m.p. 193°–4° C.

(iv) 3-(2-Aminoethyl)-N,N-dimethyl-1H-indole-5-acetamide, hydrochloride, hydrate A solution of 3-[2-(1,3-dihydro-1,3-dioxo-2H-isoindol-2-yl)ethyl]-N,N-dimethyl-1H-indole-5-acetamide (0.8 g) in ethanol (50 ml) containing hydrazine hydrate (0.53 g) was heated under reflux for 3 h. The mixture was evaporated to dryness under reduced pressure and the residue partitioned between chloroform (50 ml) and 2N sodium carbonate (50 ml). Evaporation of the dried (MgSO₄) organic phase gave a yellow gum which was dissolved in ethyl acetate containing 10% methanol (20 ml). To the solution was added ethereal hydrogen chloride and the solid which deposited was collected by filtration. This rapidly became sticky but on drying in vacuo gave the title compound as a buff foam (0.45 g) m.p. 108°–110° C., (foams).

Analysis Found: C, 56.25; H, 7.33; N, 13.73; $C_{14}H_{19}N_3O.HCl.H_2O$ Requires: C, 56.09; H, 7.40; N, 14.02%.

EXAMPLE 9

3-(2-Dimethylaminoethyl)-1H-indole-5-acetamide compound with creatinine, sulphuric acid, and water (4:4:4:7)

A mixture of 3-(2-aminoethyl)-1H-indole-5-acetamide (3.04 g) sodium hydrogen carbonate (2.88 g) and methyl iodide (8 g) in Analar methanol (25 ml) was stirred at reflux for 72 h. The reaction was cooled, filtered and evaporated to a brown oily paste which was taken up in ethanolamine (20 ml) and heated to 200° C. After 30 min the dark brown mixture was cooled, diluted with saturated aqueous sodium hydrogen carbonate solution (50 ml) and extracted with ethyl acetate (3×100 ml). The combined extracts were dried (MgSO$_4$) filtered and evaporated in vacuo to an orange-yellow oil (0.5 g).

The oil was purified by column chromatography on silica gel (Merck Type 60, 40 g) eluting with methanol-chloroform (1–10%) and 10% aqueous methanol. The oily residue was dissolved in dichloromethane, filtered and evaporated to a viscous oil (86.5 mg). The oil was dissolved in acetone (10 ml) and a 2M solution of creatinine and sulphuric acid (0.17 ml) (1:1) in water was added. An oil separated. Water was added to the mixture until a solution was obtained. Addition of more acetone did not precipitate a solid. The mixture was evaporated to dryness and then dried in vacuo. A foam was produced which was collected and boiled in acetone. The resulting solid was dried to afford the title compound (0.07 g), m.p. 122°–128°.

Analysis Found: C, 43.82; H, 6.34; N, 17.71; $C_{14}H_{19}N_3O.C_4H_7N_3O.H_2SO_4.1.75H_2O$ requires: C, 44.29; H, 6.50; N, 17.22%.

EXAMPLE 10

3-(2-Aminoethyl)-1-methyl-1H-indole-5-acetamide, hydrochloride, hemihydrate (i) 3-[2-(1,3-Dihydro-1,3-dioxo-2H-isoindol-2-yl)ethyl]-1-methyl-1H-indole-5-acetamide Sodium hydride (80% dispersion in oil) (0.14 g) was added to a solution of 3-[2-(1,3-dihydro-1,3-dioxo-2H-isoindol-2-yl)ethyl]-1H-indole-5-acetamide (1.5 g) in dry dimethylformamide (10 ml). After stirring the red solution for 30 min, methyl iodide (0.41 ml) was added and the mixture was stirred for a further 16 h. Water (40 ml) was added, the solid collected by filtration and crystallised from propan-2-ol to give the title compound as a yellow powder (1.25 g), m.p. 200°–2° C.

(ii) 3-(2-Aminoethyl)-1-methyl-1H-indole-5-acetamide, hydrochloride, hemihydrate A solution of 3-[2-(1,3-dihydro-1,3-dioxo-2H-isoindol-2-yl)ethyl]-1-methyl-1H-indole-5-acetamide (1.0 g) in ethanol (100 ml) containing hydrazine hydrate (0.72 g) was heated under reflux for 4 h. The mixture was evaporated under reduced pressure yielding a white solid. This was suspended in ethyl acetate (250 ml) and washed with saturated potassium carbonate solution (50 ml). The aqueous phase was separated and washed with a further portion of ethyl acetate (100 ml). The combined organic extracts were dried (Na$_2$SO$_4$) and evaporated under reduced pressure. Ethyl acetate containing 10% methanol (20 ml) was added to the residue and ethereal hydrogen chloride was added until no more solid deposited. Crystallisation from ethyl acetate-methanol gave the title compound as buff prisms (0.47 g) m.p. 220°–2° C.

Analysis Found: C, 56.07; H, 6.53; N, 15.29; $C_{13}H_{17}N_3O.HCl.0.5H_2O$ requires: C, 56.41; H, 6.91; N, 15.18%.

EXAMPLE 11

3-(2-Aminoethyl)-2-methyl-1H-indole-5-acetamide compound with acetic acid and water (4:4:1)

Freshly distilled 5-chloro pentan-2-one (2.35 ml) was added to a stirred suspension of 60% pure 2-(4-hydrazinophenyl)acetamide, hydrochloride (5 g, contains 0.015 mol) with sodium acetate (4.1 g) in 8% aqueous methanol (80 ml) at reflux. The reaction was heated at reflux with stirring for 3 h. The white solid which precipitated on cooling was filtered off and discarded. The mother liquors were evaporated to dryness in vacuo to afford a yellow oil.

The oil was purified by column chromatography on silica (Merck Kieselgel 60; 80 g) using 10% methanol in chloroform as eluent, to afford a pinkish brown solid. This solid was recrystallised twice from methanol-ether to afford a pale fawn solid (1.6 g).

This material was dissolved in methanol and glacial acetic acid (8 drops). The title compound crystallised as the acetate salt on addition of ether. The first crop was washed with ether to give the title compound as fawn solid (0.32 g), m.p. 169°–171°.

Analysis Found: C, 60.91; H, 7.19; N, 13.89; $C_{13}H_{17}N_3O.C_2H_4O_2.0.25H_2O$ requires: C, 60.89; H, 7.33; N, 14.20%.

EXAMPLE 12

3-(2-Aminoethyl)-α-methyl-1H-indole-5-acetamide compound with hydrogen chloride and ethanol (3:3:1)

(i) 2-(4-Nitrophenyl)propionamide

A solution of methyl 2-(4-nitrophenyl)propionate (20.0 g) in aqueous ammonia (d=0.88, 350 ml) was stirred at room temperature for 36 h. The resultant solid was collected and dried in vacuo at 50° to give the title compound (13.4 g). A sample (0.1 g) was crystallised from water to give analytically pure material m.p. 120°–121°.

(ii) 2-(4-Aminophenyl)propionamide 2-(4-Nitrophenyl)propionamide (5.3 g) in ethanol (250 ml) was hydrogenated over palladium oxide on charcoal (5%, 0.5 g) at atmospheric pressure. The reaction was terminated after 1775 ml of hydrogen had been absorbed and the catalyst was removed by filtration. Removal of the solvent gave the title compound as a white solid (4.5 g), m.p. 120°–122°.

(iii) 3-[2-(1,3-Dihydro-1,3-dioxo-2H-isoindol-2-yl)ethyl]-α-methyl-1H-indole-5-acetamide An ice-cold solution of sodium nitrite (2.0 g) in water (4 ml) was added dropwise over 10 min to a rapidly stirred ice-cold suspension of 2-(4-aminophenyl)propionamide (4.4 g) in concentrated hydrochloric acid (15 ml). The reaction mixture was stirred for an additional 15 min, and was then poured into a suspension of stannous chloride (30.5 g) in concentrated hydrochloric acid, which was maintained at −3° to −1° C. during the addition, and then for a further 20 min. The solution was neutralised with aqueous sodium carbonate (2N), and evaporated to dryness in vacuo. The resulting solid was stirred with ethanol for 20 min, the undissolved solid was filtered off and the solvent removed in vacuo. The pale yellow product was dissolved in methanol (5 ml), and ethereal hydrogen chloride (2 ml) was added. The solution was diluted with ether (100 ml), to give the phenylhydrazine hydrochloride as a purple solid (1.6 g) which was filtered off and dried at 60° C./1.0 torr for 18 h.

This crude product was dissolved in aqueous acetic acid (2N, 100 ml), and 4-(1,3-dihydro-1,3-dioxo-2H-isoindol-2-yl)butanal diethyl acetal (2.1 g) was added. The mixture was heated to reflux for 1 h. The solution was then cooled, and partitioned between water (20 ml) and ethyl acetate (200 ml). The organic layer was separated, washed with water (150 ml) and aqueous sodium bicarbonate (2N, 150 ml), and dried ($Na_2SO_4$). The solvent was removed in vacuo to give a yellow semi-solid (1.2 g) which was chromatographed over Kieselgel 60 (100 g) using ethyl acetate as eluant. The title compound crystallised from ethanol as yellow microcrystals (0.5 g) m.p. 202.5°–204° C.

(iv) 3-(2-Aminoethyl)-α-methyl-1H-indole-5-acetamide compound with hydrogen chloride and ethanol (3:3:1)

3-[2-(1,3-Dihydro-1,3-dioxo-2H-isoindol-2-yl)ethyl]-α-methyl-1H-indole-5-acetamide (0.4 g) and hydrazine hydrate (0.29 g) in ethanol (35 ml) were heated to reflux for 3 h. The solution was cooled, and the solvent was evaporated in vacuo. The solid was partitioned between a mixture of ethyl acetate (20 ml), saturated potassium carbonate solution (20 ml), and water (10 ml). The aqueous layer was separated, and extracted with a further portion of ethyl acetate (30 ml). The combined organic extracts were dried ($Na_2SO_4$) and the solvent was evaporated in vacuo to give a pale yellow oil (0.15 g). The oil was dissolved in warm ethanol (1 ml), and was treated with ethereal hydrogen chloride (0.5 ml). The solution was diluted with ether (50 ml), and the resultant solid was filtered off and dried at 60° C./0.1 torr for 18 h to give the title compound (0.12 g) m.p. 102°–105° (foams).

Analysis Found: C, 58.3; H, 6.8; N, 14.9; $C_{13}H_{17}N_3O.HCl0.3EtOH$ requires: C, 58.0; H, 7.1; N, 14.9%.

EXAMPLE 13

3-(2-Amino-1-methylethyl)-1H-indole-5-acetamide, compound with fumaric acid, water and ethyl acetate (1:0.5:1:0.2)

(i) 1-Acetyl-2,3-dihydro-1H-indole-5-acetic acid, methyl ester

To a suspension of thallium (III) nitrate supported on Montmorillonite clay (100 g) (0.066 mol) in chloroform (250 ml) was added a solution of 1,5-diacetyl-2,3-dihydroindole (12.6 g) in chloroform (50 ml) and the resulting mixture was stirred at 45°–50° for 1 h. It was then filtered and the filter cake was washed thoroughly with chloroform (300 ml). The combined filtrate and washings were washed with dilute hydrochloric acid (2N, 250 ml), water (250 ml) and sodium bicarbonate (250 ml), dried ($MgSO_4$) and evaporation of the solvent gave a crude product (14 g). Crystallisation from ethyl acetate-ether gave the title compound (10.2 g), m.p. 110°–111°.

(ii) 1-Acetyl-1H-indole-5-acetic acid, methyl ester

An intimate mixture of 1-acetyl-2,3-dihydro-1H-indole-5-acetic acid, methyl ester (2.96 g) and 10% palladium on charcoal (50% moistened with water) (6.18 g) was heated at 200° for 1½ h and the resulting solid was continuously extracted with chloroform (Soxhlet) for 2 h. Evaporation of the solvent gave an oil (1.21 g), which was purified by column chromatography on silica (Merck 7734; 138 g). Elution with ether-petroleum ether (1:1) gave the title compound (0.99 g) as an oil which was used in the next stage without further purification.

(iii) 1H-Indole-5-acetamide

A solution of 1-acetyl-1H-indole-5-acetic acid, methyl ester (1.46 g) in methanol (10 ml) and conc. ammonium hydroxide (20 ml) was stirred at ambient temperature for 48 h. The resulting solution was poured into ethyl acetate (100 ml). The layers were separated and the aqueous layer was washed with ethyl acetate (3×50 ml) and chloroform (3×50 ml). The organic layers were dried ($MgSO_4$) and the solvent was evaporated to give a solid (0.72 g). Crystallisation from ethyl acetate gave the title compound as a white solid, (0.3 g) m.p. 146°–7°.

(iv) 3-(1-Methyl-2-nitroethyl)-1H-indole-5-acetamide

A mixture of 1H-indole-5-acetamide (0.41 g) and 1-nitropropene (0.23 g) was heated at 80° for 24 h and then left at ambient temperature for another 24 h. Chromatography of the thick oil on silica (Merck 7734, 35 g) eluting with ethyl acetate gave a mixture of the title compound and starting material (4:1, 0.26 g) which was used in the next stage without further purification.

(v) 3-(2-Amino-1-methylethyl)-1H-indole-5-acetamide, compound with fumaric acid, water and ethyl acetate (1:0.5:1:0.2)

3-(1-Methyl-2-nitroethyl)-1H-indole-5-acetamide (0.24 g) crude was hydrogenated over pre-reduced 10% palladium oxide on charcoal (50% moistened with water, 0.24 g) in ethanol (50 ml) until the theoretical amount of hydrogen was absorbed. The catalyst was removed by filtration through Hyflo and evaporation of the solvent gave 0.15 g of a colourless oil which was purified by column chromatography on Merck-Aluminium oxide (neutral (1077), 5 g) eluting with ethyl acetate and ethyl acetate:isopropanol:water (25:15:8:2). An oil (0.1 g) was obtained which was taken up in ethanol and treated with fumaric acid (50 g). Removal of the solvent gave an oil which on trituration with ethyl acetate-ethanol afforded the title compound as an off white solid (70 mg) m.p. 190°–192°.

Analysis Found: C, 58.0; H, 6.0; N 11.96% $C_{13}H_{17}N_3O.0.5C_4H_4O_4.H_2O.0.4EtOAc$ Requires: C, 58.0; H, 7.12; N, 12.27%.

EXAMPLE 14

3-(1-Aminoethyl)-1H-indole-5-acetamide, hydrochloride

Method A

A solution of 2-(4-hydrazinophenyl)acetamide hydrochloride (0.5 g) and 4-chlorobutanal diethylacetal (0.39 g) in methanol (45 ml) and water (5 ml) containing acetic acid (1.5 ml) and sodium acetate (0.5 g) was heated at reflux for 16 h. After cooling, the solution was concentrated under vacuum and the residue was partitioned between ethyl acetate (25 ml) and saturated potassium carbonate solution (35 ml). The aqueous portion was extracted with ethyl acetate (2×30 ml) and the combined organic extracts were dried and concentrated under vacuum to afford the title compound as a brown solid.

TLC. Silica, ethyl acetate-propan-2-ol-water-0.88 NH$_3$ (25:15:8:2) showed one product with R$_f$=0.4 identical with that of a sample prepared by the method of Example 1.

Method B (i) 4-[-(4-Chlorobutylidene)hydrazino]benzeneacetamide, compound with ethanol (10:3)

A solution of 2-(4-hydrazinophenyl)acetamide hydrochloride (0.9 g) and 4-chlorobutanal diethylacetal (0.85 g) in aqueous acetic acid (b 50%, 50 ml) was heated at 50° for 90 min. After cooling, the solution was cautiously poured onto sodium bicarbonate (60 g) before the addition of ethyl acetate (60 ml) and water (100 ml). After separation, the aqueous portion was further extracted with ethyl acetate (2×50 ml) and the combined organic extracts were washed with sodium bicarbonate (8%, 3×60 ml), brine (10%, 2×50 ml), dried and concentrated under vacuum to afford an orange solid (1.1 g). Column chromatography (Kieselgel G, 35 g) with 2% methanol/chloroform as eluent afforded the title hydrazone (0.62 g) as an orange solid. A sample for analysis was recrystallised from isopropanol, m.p. 106°–112°.

(ii) 3-(2-Aminoethyl)-1H-indole-5-acetamide

A solution of 4-[2-(4-chlorobutylidene)hydrazino]benzeneacetamide (0.3 g) in methanol (45 ml) and water (5 ml) was heated at reflux for 15 h. After cooling, the solution was concentrated under vacuum to afford a brown semi-solid (0.29 g) which was partitioned between ethyl acetate (20 ml) and saturated potassium carbonate solution (20 ml). Concentration of the organic portion under vacuum afforded the crude title compound as a brown oil (0.18 g).

TLC.Silica, ethyl acetate-propan-2-ol-water-0.88 ammonia (25:15:8:2) showed one basic product R$_f$=0.4 identical with a sample prepared by the method of Example 1.

EXAMPLE 15

3-(2-Aminoethyl)-N-methyl-1H-indole-5-acetamide, hydrochloride

A mixture of 2-(4-hydrazinophenyl)-N-methyl acetamide (0.43 g) and 4-chlorobutanal dimethyl acetal (93%, 0.33 g) was heated under reflux in aqueous ethanol (1:5, 30 ml) for 20 h. Solvent was removed in vacuo and the residue re-evaporated with propan-2-ol (3×20 ml). Recrystallisation of the residue from ethyl acetate-methanol (2:1, 15 ml) gave the title compound as an off-white powder (0.19 g), m.p. 230°–234°.

TLC.Silica, ethyl acetate-propan-2-ol-water-0.88 ammonia (25:15:8:2) showed this material contained a product R$_f$=0.28 identical with a sample prepared by the method of Example 3.

EXAMPLE 16

3-[2-(1,3-Dihydro-1,3-dioxo-2H-isoindol-2-yl)ethyl]-1H-indole-5-acetamide (i) 4-Hydrazinophenylacetonitrile A solution of sodium nitrite (1.9 g) in water (16 ml) was added dropwise to a suspension of 4-aminophenylacetonitrile (3.6 g) in concentrated hydrochloric acid (37 ml) so that the temperature did not exceed +2° C. The resulting mixture was stirred overnight (room temperature), the yellow solid collected, washed with cold ethanol (20 ml) and ether (50 ml), dried (vacuum) to give the title compound as a yellow solid.

This material was used in the next step without further purification (ii) 3-[2-(1,3-Dihydro-1,3-dioxo-2H-isoindol-2-yl)ethyl]-1Hindole-5-acetonitrile A mixture of 4-hydrazino phenylacetonitrile hydrochloride (3.15 g) and 4-(1,3-dihydro-1,3-dioxo-2H-isoindol-2-yl)butanal diethyl acetal (4.95 g) in acetic acid (25%, 150 ml) was refluxed for 2 h, cooled to 25°, precipitate filtered, washed with water (2×20 ml) and ether (100 ml). The crude product was obtained as a dark solid (4.5 g) which was triturated with ethyl acetate to give the title compound (3.16 g) m.p. 185°–186°.

(iii) 3-[2-(1,3-Dihydro-1,3-dioxo-2H-isoindol-2-yl)ethyl]-1H-indole-5-acetamide

A solution of 3-[2-(1,3-dihydro-1,3-dioxo-2H-isoindol-2-yl)ethyl]-1H-5-acetonitrile (0.2 g) in concentrated hydrochloric acid (5 ml) and glacial acetic acid (2 ml) was stirred at 40°–50° for 3 h.

TLC Polygram silica, 5% methanol/methylene chloride showed a single new product with R$_f$0.13 identical with that of a sample prepared by the method of Example 2 (ii).

EXAMPLE 17

3-(2-Aminoethyl)-N-cyclohexyl-1H-indole-5-acetamide, compound with maleic acid (1:1)

(i) N-Cyclohexyl-3-[2-(1,3-dihydro-1,3-dioxo-2H-isoindol-2-yl)ethyl]-1H-indole-5-acetamide A solution of 3-[2-(1,3-dioxo-2H-isoindol-2-yl)ethyl]-1H-indole-5-acetic acid (0.2 g) and triethylamine (0.061 g) in chloroform (10 ml) was treated with isobutylchloroformate (0.08 g) at −5°, resulting red solution stirred at the same temperature for 20 h and cyclohexylamine was added to the resulting anhydride (0.06 g). Reaction was allowed to warm up to ambient temperature and stirred for 1 h then the mixture was poured into dilute hydrochloric acid (2N, 20 ml) extracted with chloroform (3×10 ml), dried (MgSO$_4$), solvent removed and residual oil purified by chromatography (silica Merck, 7734; 10 g; 1% methanol in dichloromethane as eluent). Product was obtained as an oil which on treatment with ethyl acetate/ether gave the title compound as a solid (0.09 g) m.p. 175°–6°.

(ii) 3-(2-Aminoethyl)-N-cyclohexyl-1H-indole-5-acetamide, compound with maleic acid (1:1)

N-cyclohexyl-3-[2-(1,3-dihydro-1,3-dioxo-2H-isoindol-2-yl)ethyl]-1H-indole-5-acetamide (0.39 g) in abs. ethanol (15 ml) was treated with hydrazine hydrate (0.15 g) and the reaction mixture heated at reflux for 1.5 h. All the solvent was removed in vacuo and the residual solid was partitioned between ethyl acetate and saturated potassium carbonate (20 ml). The aqueous layer was extracted with ethyl acetate (4×50 ml), the extract dried (MgSO$_4$) and the solvent removed. The residual oil was dissolved in absolute ethanol (20 ml) and a solution of maleic acid (0.1 g) in absolute ethanol (5 ml) was added, solvent removed in vacuo and the residual semi-solid crystallised from ethanol/ethyl acetate/ether to give the title compound as a white solid (0.057 g), m.p. 140°–140.5°.

Analysis Found: C, 62.98; H, 6.97; N, 9.78; C$_{18}$H$_{25}$N$_3$O.C$_4$H$_4$O$_4$. requires: C, 63.60; H, 7.04; N, 10.11%.

EXAMPLE 18

3-(2-Aminoethyl)-N-(2-propenyl)-1H-indole-5-acetamide, compound with maleic acid (1:1)

(i)a 3-[2-(1,3-dihydro-1,3-dioxo-2H-isoindol-2-yl)ethyl]-N-(2-propenyl)-1H-indole-5-acetamide A solution of 3-[2-(1,3-dihydro-1,3-dioxo-2H-isoindol-2-yl)ethyl]-1H-indole-5-acetic acid (1.0 g) and triethylamine (0.3 g) in chloroform (5 ml) was treated with 2-chloro-1-methylpyridinium iodide (0.75 g) under nitrogen and stirred at room temperature for 1 h. To this solution was added allylamine (0.11 g) and triethylamine (0.27 ml) and stirring continued for 3 h. The mixture was poured into dilute hydrochloric acid (10 ml) and extracted with chloroform (3×30 ml). The combined extracts were dried (MgSO$_4$) and concentrated. The residual oil was purified by chromatography on silica (Merck 7734, 40 g) eluting with 1% methanol in dichloromethane to give a foam. Trituration of this material with ether gave the title compound as a yellow solid (0.22 g) m.p. 162°–163°.

The following compounds were similarly prepared from 3-[2-(1,3-dihydro-1,3-dioxo-2H-isoindol-2-yl)ethyl]-1H-indole-5-acetic acid (A) and the appropriate amine:

(i)b Morpholine (0.165 g) and A (1.0 g) gave 4[[3-[2-(1,3-dihydro-1,3-dioxo-2H-isoindol-2-yl)ethyl]-1H-indol-5-yl]acetyl]morpholine as a yellow solid (0.2 g) m.p. 140°–141°.

(i)c Benzylamine (0.2g) and A (1.0 g) gave 3-[2-(1,3-dihydro-1,3-dioxo-2H-isoindol-2-yl)ethyl]-N-(phenylmethyl)-1H-indole-5-acetamide as a colourless solid (0.2 g) m.p. 165°–166°.

(ii)a 3-(2-Aminoethyl)-N-(2-propenyl)-1H-indole-5-acetamide, compound with maleic acid (1:1)

A solution of 3-[2-(1,3-dihydro-1,3-dioxo-2H-isoindol-2-yl)ethyl]-N-(2-propenyl)-1H-indole-5-acetamide (0.49 g) in absolute ethanol (10 ml) was treated with hydrazine hydrate (0.2 g) and the mixture was heated at reflux for 2 h. Removal of the solvent gave a white solid which was partitioned between dilute potassium carbonate and chloroform. The aqueous layer was extracted with chloroform (3×30 ml). The extracts were dried and concentrated. The residue (0.35 g) in absolute ethanol (5 ml) was treated with maleic acid (0.15 g) in ethanol and concentrated. Recrystallisation of the residue from ethanol-ethyl acetate gave the title compound as a white solid (0.28 g), m.p. 120°–121°.

The following compounds were similarly prepared:

(ii)b 4-[[3-(2-Aminoethyl)-1H-indol-5-yl]acetyl]morpholine compound with creatinine, sulphuric acid and water (1:1:1:1) (0.45 g) m.p. 232°–238°, from 4-[[3-[2-(1,3-dihydro-1,3-dioxo-2H-isoindol-2-yl)ethyl]-1H-indol-5-yl]acetyl]morpholine (0.7 g) and hydrazine hydrate (0.3 g).
Analysis Found: C, 46.50; H, 6.15; N, 16.23; C$_{16}$H$_{21}$N$_3$O.C$_4$H$_7$N$_3$O.H$_2$SO$_4$.H$_2$O requires: C, 46.50; H, 6.24; N, 16.27%.

(ii)c 3-(1-Aminoethyl)-N-(phenylmethyl)-1H-indole-5-acetamide, compound with creatinine, sulphuric acid and water (1:7:4:4) (0.042 g) m.p. 234° (dec.) from 3-[2-(1,3-dihydro-1,3-dioxo-2H-isoindol-2-yl)ethyl]-N-(phenyl methyl)-1H-indole-5-acetamide (0.225 g) and hydrazine hydrate (0.091 g).
Analysis Found: C, 36.12; H, 5.2; N, 22.1%; C$_{19}$H$_{21}$N$_3$O.7C$_4$H$_7$N$_3$O.4H$_2$SO$_4$.4H$_2$O requires: C, 36.1; H, 5.54; N, 21.5%.

EXAMPLE 19

3-(2-Dimethylaminoethyl)-1H-indole-5-acetamide

A mixture of 4-chlorobutanal (1.8 g) and 2-(4-hydrazinophenyl)acetamide hydrochloride (3 g) in 50% aqueous acetic acid (200 ml) was heated at reflux for 45 min., then cooled and evaporated to give 3-(2-chloroethyl)-1H-indole-5-acetamide as a dark organe-brown foam. $\tau$ (DMSO) 6.3(2H); 6,8(2H); (CH$_2$CH$_2$Cl)

The foam was dissolved in Analar ethanol (50 ml) and anhydrous dimethylamine (10 ml) was added steadily over 2 min. The solution was stirred at room temperature for 16 h, evaporated to dryness, and the residue partitioned between 8% aqueous sodium hydrogen carbonate (125 ml) and ethyl acetate (100 ml). The organic layer was extracted with 2N hydrochloric acid which was shown by t.l.c. silica, ethyl acetate, i-propanol, water, ammonia: 25:15:8:2 to contain a major component R$_f$ 0.5 identical with that of a sample of 3-(2-dimethylaminoethyl)-1H-indole-5-acetamide prepared by the method of Example 9.

EXAMPLE 20

3-[2-(Ethylamino)ethyl]-1H-indole-5-acetamide, compound with hydrogen chloride (1:1)

A solution of 3-(2-aminoethyl)-1H-indole-5-acetamide (0.8 g) in absolute ethanol (20 ml) was treated with acetaldehyde (0.67 g) at room temperature with stirring for 30 min. Sodium borohydride (0.15 g) was added and the mixture was stirred for an additional 30 mim. The solvent was evaporated in vacuo to give a gel-like residue which was chromatographed over Kieselgel 60 (80 g) using mixtures of ammonia (d=0.88) in methanol 0–1%. The appropriate fractions were collected and evaporated in vacuo and the residue was dissolved in ethanol (3 ml), filtered, and treated with ethereal hydrogen chloride (1 ml). The mixture was diluted with dry ether (30 ml), and the resultant solid filtered off. The product was washed with ether (2×20 ml), and dried at 60° in vacuo to give the title compound (0.16 g) m.p. 105°–113°.

Analysis Found: C, 59.6; H, 7.0; N, 13.4; C$_{14}$H$_{13}$N$_3$O.HCl requires: C, 59.7; H, 7.2; N, 14.9%.

EXAMPLE 21

3-(2-Aminoethyl)-1H-indole-5-thioacetamide (i) 3-[2-[[(Phenylmethoxy)Carbonyl]amino]ethyl]-1H-indole-5-acetamide A solution of 3-[2-(1,3-dihydro-1,3-dioxo-2H-isoindol-2-yl)ethyl]-1H-indole-5-acetamide (17.55 g) and hydrazine hydrate (12 ml) in ethanol (700 ml) was heated at reflux for 2 h. The resulting suspension was cooled to ambient temperature and all the solvent was evaporated in vacuo. The resulting yellow solid was dissolved in dilute sodium hydroxide (250 ml) and tetrahydrofuran (100 ml) and treated with benzylchloroformate (21 ml) at 5°. Stirring was continued for 1 h at ambient temperature, reaction mixture extracted with ethylacetate (4×200 ml), dried (MgSO$_4$) and solvent removed to give crude product as an oil which on trituration with ethylacetate gave the title compound as a white solid (6.4 g) m.p. 124°–5°.

(ii) 3-[2-[[(Phenylmethoxy)carbonyl]amino]ethyl]-1H-indole-5-thioacetamide

A mixture of 3-[2[[(Phenylmethoxy)carbonyl]amino]ethyl]-1H-indole-5-acetamide (1.2 g) and phosphorus pentasulphide (0.21 g) in benzene (70 ml) was heated at reflux for 40 min. The resulting suspension was poured onto saturated ammonium chloride (20 ml) extracted with chloroform (3×40 ml), organic layer dried (MgSO$_4$) and solvent removed. Column chromatography (Merch 7734, 70 g) eluting with 1% methanondichloromethane gave an oil which was triturated with ethylacetate to give the title compound as a white solid (0.18 g) m.p. 126°–7°.

Analysis Found: C, 6416; H, 5.74; N, 10.81; C$_{20}$H$_{21}$N$_3$O$_2$S. 0.3 C$_4$H$_8$O$_2$Reg. C, 64.64; H, 5.99; N, 10.67.

(iii) 3-(2-Aminoethyl)-1H-indole-5-thioacetamide

A solution of 3-[2-[[(Phenylmethoxy)carbonyl]amino]ethyl]-1H-indole-5-thioacetamide (0.15 g) in glacial acetic acid saturated with hydrobromide (5 ml) was stirred at 10° for 1 h.

TLC Polygram silica, ethylacetate, iso-propanol, water, ammonia-25:15:8:2 indicates that deprotection has been completed. R$_f$0.4.

PHARMACEUTICAL EXAMPLES

Tablets

These may be prepared by direct compression or wet granulation. The direct compression method is preferred but may not be suitable in all cases as it is dependent upon the dose level and physical characteristics of the active ingredient.

| A. Direct Compression | |
|---|---|
| | mg/tablet |
| Active ingredient | 10.0 |
| Microcrystalline Cellulose B.P.C. | 89.5 |
| Magnesium Stearate | 0.5 |
| | 100.0 |

The active ingredient is sieved through a 250 μm sieve, blended with the excipients and compressed using 6.0 mm punches. Tablets of other strengths may be prepared by altering the compression weight and using punches to suit.

| B. Wet Granulation | |
|---|---|
| | mg/tablet |
| Active ingredient | 10.0 |
| Lactose B.P. | 74.5 |
| Starch B.P. | 10.0 |
| Pregelatinised Maize Starch B.P. | 5.0 |
| Magnesium Stearate B.P. | 0.5 |
| Compression Weight | 100.0 |

The active ingredient is sieved through a 250 μm sieve and blended with the lactose, starch and pregelatinised starch. The mixed powders are moistened with purified water, granules are made, dried, screened and blended with the Magnesium Stearate. The lubricated granules are compressed into tablets as described for the direct compression formulae.

The tablets may be film coated with suitable film forming materials, e.g. methyl cellulose or hydroxypropyl methyl cellulose using standard techniques. Alternatively the tablets may be sugar coated

| Capsules | mg/capsule |
|---|---|
| Active ingredient | 10.0 |

| -continued | |
|---|---|
| Capsules | mg/capsule |
| *Starch 1500 | 89.5 |
| Magnesium Stearate B.P. | 0.5 |
| Fill Weight | 100.0 |

*A form of directly compressible starch supplied by Colorcon Ltd., Oprington, Kent.

The active ingredient is sieved through a 250 μm sieve and blended with the other materials. The mix is filled into No. 2 hard gelatin capsules using a suitable filling machine. Other doses may be prepared by altering the fill weight and if necessary changing the capsule size to suit.

| Syrup | mg/5 ml dose |
|---|---|
| Active ingredient | 10.0 |
| Sucrose B.P. | 2750.0 |
| Glycerine B.P. | 500.0 |
| Buffer | |
| Flavour | |
| Colour | as required |
| Preservative | |
| Distilled Water | 5.00 ml |

The active ingredient, buffer, flavour, colour and preservative are dissolved in some of the water, and the glycerine is added. The remainder of the water is heated to 80° C. and the sucrose is dissolved in this and cooled. The two solutions are combined, adjusted to volume and mixed. The syrup produced is clarified by filtration.

| Suppositories | |
|---|---|
| Active ingredient | 10.0 mg |
| *Witepsol H15 to | 1.0 g |

A suspension of the active ingredient in the matter Witepsol H15 is prepared and filled using a suitable machine into 1 g size suppository moulds.

| Injection for Intravenous Administration | |
|---|---|
| | % w/v |
| Active ingredient | 0.20 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

| INHALATION CARTRIDGES | |
|---|---|
| | mg/cartridges |
| Active ingredient micronised | 1.00 |
| Lactose B.P. | 39.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler (e.g. Glaxo Rotahaler).

| METERED DOSE PRESSURISED AEROSOL | | |
| --- | --- | --- |
| | mg/metered dose | Per can |
| Active ingredient micronised | 0.500 | 120 mg |
| Oleic Acid B.P. | 0.050 | 12 mg |
| Trichlorofluoromethane B.P. | 22.25 | 5.34 mg |
| Dichlorodifluoromethane B.P. | 60.90 | 14.62 g |

The active ingredient is micronised in a fluid energy mill to a fine particle size range. The Oleic Acid is mixed with the Trichlorofluoromethane at a temperature of 10°–15° C. and the micronised drug is mixed into this solution with a high shear mixer. The suspension is metered into aluminium aerosol cans and suitable metering valves, delivering a metered dose of 85 mg of suspension are crimped onto the cans and the Dichlorodifluoromethane is pressure filled into the cans through valves.

We claim:

1. A compound of the formula (I):

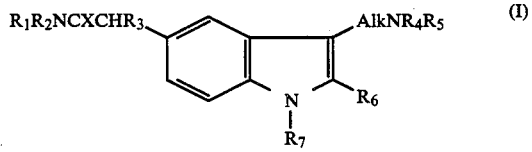

wherein
$R_1$, $R_3$, $R_4$, $R_6$ and $R_7$, which may be the same or different, each represent a hydrogen atom or a $C_{1-6}$ alkyl group;
$R_2$ represents a hydrogen atom or a $C_{1-6}$ alkyl, aryl, $arC_{1-4}alkyl$ $C_{5-7}$ cycloalkyl or $C_{3-6}$ alkenyl group;
or $R_1$ and $R_2$, together with the nitrogen atom to which they are attached, for a saturated monocyclic 5 to 7-membered ring;
$R_5$ represents a hydrogen atom or a $C_{1-6}$ alkyl or $C_{3-6}$ alkenyl group;
or $R_4$ and $R_5$ together form an aralkylidene group;
Alk represents an alkylene chain containing two or three carbon atoms which may be unsubstituted or substituted by not more than two $C_{1-3}$ alkyl groups; and
X represents an oxygen or sulphur atom;
Aryl, alone or as part of a group means phenyl which may be optionally substituted with one or more substitutes selected from the group consisting of $C_{1-6}$ alkyl, $C_{1-6}$ alkoxy and halogen atoms;
and physiologically acceptable salts and solvates thereof.

2. A compound according to claim 1, wherein $R_1$ represents a hydrogen atom and $R_2$ represents a hydrogen atom or an alkyl group containing 1 to 3 carbon atoms.

3. A compound according to claim 1, wherein $R_3$ represents a hydrogen atom.

4. A compound according to claim 1, wherein Alk represents an unsubstituted alkylene group containing two carbon atoms.

5. A compound according to claim 1, wherein $R_4$ and $R_5$, which may be the same or different, each represents a hydrogen atom or a methyl or ethyl group and $R_6$ and $R_7$, each represents a hydrogen atom.

6. A compound according to claim 1, wherein $R_1$ represents a hydrogen atom, $R_2$ represents a hydrogen atom or alkyl group containing one to three carbon atoms, $R_3$ represents a hydrogen atom, Alk represents an unsubstituted alkylene group containing two carbon atoms, $R_4$ and $R_5$, which may be same or different, each represent a hydrogen atom, a methyl or ethyl group and $R_6$ and $R_7$ each represents a hydrogen atom.

7. A compound according to claim 1 having the formula (Ia):

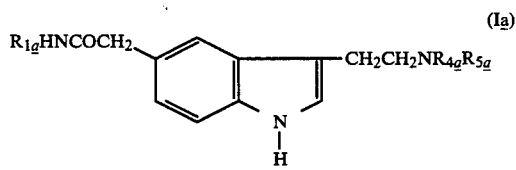

wherein
$R_{1a}$ represents a hydrogen atom or an alkyl group containing 1 to 4 carbon atoms;
$R_{4a}$ and $R_{5a}$, which may be the same or different, each represents a hydrogen atom or a methyl or ethyl group such that the total number of carbon atoms in $R_{4a}$ and $R_{5a}$ together does not exceed two, or together $R_{4a}$ and $R_{5a}$ represent a benzylidene group;
and physiologically acceptable salts and solvates thereof.

8. A compound selected from 3-(2-aminoethyl)-1H-indole-5-acetamide and 3-(2-aminoethyl)-N-methyl-1H-indole-5-acetamide and their physiologically acceptable salts solvates.

9. A compound according to claim 1, wherein the physiologically acceptable salt is a hydrochloride, hydrobromide, sulphate, fumarate or a maleate.

10. A compound according to claim 8 wherein the physiologically acceptable salt is a hydrochloride, hydrobromide, sulphate, fumarate or a maleate.

* * * * *